United States Patent
Tzeng et al.

Patent Number: 5,646,164
Date of Patent: Jul. 8, 1997

[54] α-METHYLENE-γ-BUTYROLACTONES: NEW INHIBITORS OF PLATELET AGGREGATION

[75] Inventors: Cherng-Chyi Tzeng; Yeh-Long Chen; Tai-Chi Wang, all of Kaohsiung; Che-Ming Teng, Taipei, all of Taiwan

[73] Assignee: National Science Council, Taipei, Taiwan

[21] Appl. No.: 557,268

[22] Filed: Nov. 14, 1995

[51] Int. Cl.$^6$ ............ C07D 405/12; C07D 407/12; A61K 31/47; A61K 31/37
[52] U.S. Cl. ............ 514/314; 514/457; 546/178; 549/284
[58] Field of Search ............ 546/178; 514/314, 514/457; 549/284

*Primary Examiner*—David B. Springer
*Attorney, Agent, or Firm*—W. Wayne Liauh

[57] ABSTRACT

The present inventors have discovered three classes of novel α-methylene-γ-butyrolactones with excellent antiplatelet activity. As a result of intensive studies, it has been found that compounds represented by the formula I–III are potent inhibitors of platelet aggregation.

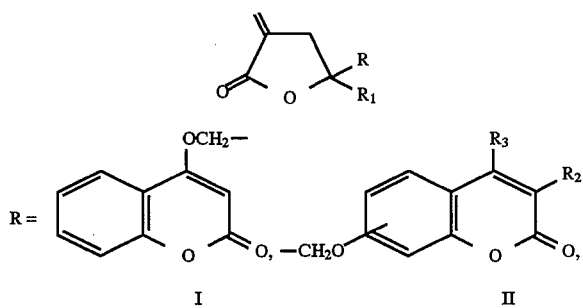

-continued

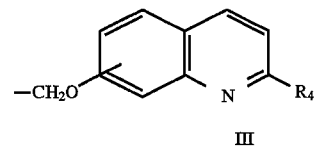

For the formula I, $R_1$ is a methyl, a phenyl group optionally substituted with one or two group selected from halide, ($C_1$–$C_4$) alkyl, ($C_1$–$C_4$) alkoxy, phenyl, nitro, amino.

For the formula II, $R_1$ is a methyl, a phenyl group optionally substituted with one or two group selected from halide, ($C_1$–$C_4$) alkyl, ($C_1$–$C_4$) alkoxy, phenyl, nitro, amino; $R_2$ represents hydrogen, halide, ($C_1$–$C_4$) alkyl, phenyl, nitro, amino; $R_3$ represents hydrogen, halide, ($C_1$–$C_4$) alkyl, phenyl, nitro, amino.

For the formula III, $R_1$ is a methyl, a phenyl group optionally substituted with one or two group selected from halide, ($C_1$–$C_4$) alkyl, ($C_1$–$C_4$) alkoxy, phenyl, nitro, amino; $R_4$ represents hydrogen, hydroxy, ($C_1$–$C_4$) alkyl.

The present invention also provides a cost-efficient method for the preparation of formula I–III.

Formula I–III may be administered orally or parenterly with an inert diluent or with a pharmaceutically acceptable carrier in the treatment or the prevention of cardiovascular disease.

5 Claims, No Drawings

α-METHYLENE-γ-BUTYROLACTONES: NEW INHIBITORS OF PLATELET AGGREGATION

TECHNICAL FIELD OF THE INVENTION

The present invention relates to the therapeutical application of antiplatelet α-methylene-γ-butyrolactones.

BACKGROUND OF THE INVENTION

Cardiovascular diseases, especially various forms of thrombosis, such as coronary, embolic, venous and traumatic thrombosis, account for a large number of death per year. In fact it is estimated by the American Heart Association that 54% of all deaths in the United States can be attributed to cardiovascular disease. It is therefore important for us to be familiar with physical, chemical and clinical aspects of drugs used to treat these form of thrombosis. Since it is believed that initiation of thrombus formation is dependent on platelet aggregation, the inhibitors of platelet aggregation could be prototypes for drugs that are more effectively combat thrombosis that leads to heart attacks and strokes. It was therefore prompted us to search for novel compounds possessing more potent inhibiting activity on platelet aggregation.

Coumarin derivatives such as bishydroxycoumarin and warfarin are the principal anticoagulants. Other clinically useful antiplatelet drugs are aspirin, eicosapentanoic acid (EPA), dipyridamole, dazoxiben, and ticlopidine. Their utilization is, however, limited by the potency and the side effects. This invention describes the preparation of α-methylene-γ-butyrolactone-containing coumarins, quinolines, and quinolinones from commercially available starting materials in an efficient route. The products describes herein are suitable for large-scale production and exhibit very strong and extensive antiplatelet activity.

DETAILED DESCRIPTION OF THE INVENTION

This invention included the preparation and the antiplatelet evaluation of novel α-methylene-γ-butyrolactones which have been proved to be potent inhibitors of platelet aggregation. These active compounds, as free type or their pharmaceutically acceptable salts, may be administered parenterally or orally in a suitable pharmaceutical form. They also may be administered along or in conjunction with other antiplatelet agents, in combination with any pharmaceutically acceptable carrier.

As used herein, the pharmaceutically acceptable salts include salts with inorganic acids, such as hydrochloride, hydrobromide, sulfate and phosphate; those organic acids, such as acetate, maleate, tartrate, methanesulfonate; and those with amino acids, such as arginine, aspartic acid and glutamic acid. Suitable pharmaceutical forms include sterile aqueous solutions or dispersions, sterile powders, tablets, troches, pills, capsules, and the like. In addition, the active compounds may be incorporated into sustained-release preparations and formulations. The pharmaceutically acceptable carrier includes any and all solvents, disintegrating agents, binders, excipients, lubricants, absorption delaying agents and the like. Although the compound of the present invention may also be present as a hydrate or as a stereoisomer, it is a matter of course that these hydrates and stereoisomers are also included in the scope of the present invention.

The new compounds can be prepared according to the following reaction schemes and protocols.

PART A
Preparation of 4-[(2, 3, 4, 5-Tetrahydro-3-methylene-2-oxo-5-furanyl) methoxy]-2H-1-benzopyran-2-ones (Scheme 1)

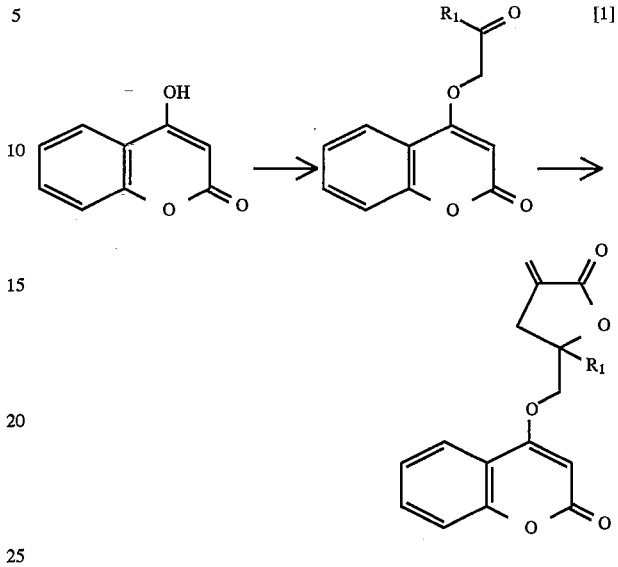

The commercially available 4-hydroxycoumarin was treated with potassium carbonate and a haloketone (chloroacetone, $R_1=CH_3$; 2-bromoacetophenone, $R_1=C_6H_5$; 2-bromo-4'-fluoroacetophenone, $R_1=C_6H_4F$; 2-bromo-4'-chloroacetophenone, $R_1=C_6H_4Cl$; 2-bromo-4'-bromoacetophenone, $R_1=C_6H_4Br$; 2-bromo-4'-iodoacetophenone, $R_1=C_6H_4I$; 2-bromo-4'-methylacetophenone, $R_1=C_6H_4CH_3$; 2-bromo-4'-nitroacetophenone, $R_1=C_6H_4NO_2$; 2-bromo-4'-methoxyacetophenone, $R_1=C_6H_4OCH_3$; 2-bromo-4'-phenylacetophenone, $R_1=C_6H_4C_6H_5$) in acetone or N,N,-dimethylformamide (DMF) to provide (2'-oxoethoxy)-2H-1-benzopyran-2-ones which were reacted with ethyl 2-(bromomethyl)acrylate in tetrahydrofuran (THF) (Reformatsky reaction) to produce 4-[(2,3,4,5-tetrahydro-3-methylene-2-oxo-5-furanyl)methoxy]-2H-1-benzopyran-2-ones (I).

EXAMPLE 1

4-[(2,3,4,5-Tetrahydro-2-methyl-4-methylene-5-oxo-2-furanyl)methoxy]-2H-1-benzopyran-2-one (1)

To a solution of 4-hydroxycoumarin (1.62 g, 10 mmol) in acetone (20 ml) were added potassium carbonate (5.53 g, 40 mmol) and chloroacetone (1.38 g, 15 mmol). The resulting mixture was refluxed for 4 h. (monitored by TLC). Evaporation of the solvent gave a residue which was poured into ice water (50 ml). The resulting solid was collected and crystallized from ethyl acetate to afford 4-(2-Oxopropoxy)-2H-1-benzopyran-2-one (1a) (1.28 g, 55.1%) as a white needle crystal. mp: 163°–165° C.; IR(KBr) $v_{max}$: 1716, 1625; UV(CHCl$_3$) $\lambda_{max}$(log ε): 305 (3.83), 266 (4.05); $^1$H-NMR (CDCl$_3$): δ2.36 (s, 3H, CH$_3$), 4.77 (s, 2H, OCH$_2$), 5.57 (s, 1H, 3-H), 7.28–7.36 (m, 2H, 6- and 8-H), 7.54–7.63 (m, 1H, 7-H), 7.88–7.94 (m, 1H, 5-H). Anal. Calcd for C$_{12}$H$_{10}$O$_4$: C, 66.05; H, 4.62. Found: C, 66.01; H, 4.64.

To a solution of 1a (0.655 g, 3 mmol) in dry tetrahydrofuran (60 ml) were added activated zinc powder (0.255 g, 3.9 mmol), hydroquinone (6 mg), and ethyl 2-(bromomethyl)acrylate (0.78 g, 4 mmol). The mixture was reflued under nitrogen atmosphere for 36 h. (monitored by TLC). After cooling it was poured into an ice-cold 5% HCl solution (300 ml) and extracted with $CH_2Cl_2$ (75 ml×3). The dichloromethane extracts were combined and washed with saline, dried over $Na_2SO_4$, and then evaporated to give a residual solid which was crystallized from ethyl acetate to afford the title compound (0.656 g, 76.4%) as a pale yellow crystal. mp: 161°–162° C.; IR(KBr) $v_{max}$: 1766, 1703, 1627; UV (CHCl$_3$) $\lambda_{max}$(log $\epsilon$): 306 (3.79), 276 (4.01), 266 (4.05); $^1$H-NMR (CDCl$_3$): δ1.64 (s, 3H, 5'-CH$_3$), 2.88 (dt, 1H, 4'-H), 3.19 (dt, 1H, 4'-H), 4.08, 4.20 (two d, 2H, OCH$_2$), 5.67 (s, 1H, 3-H), 5.75 (t, 1H, vinylic H), 6.38 (t, 1H, vinylic H), 7.12–7.33 (m, 2H, 6 and 8-H), 7.51–7.65 (m, 2H, 5 and 7-H). Anal. Calcd for $C_{16}H_{14}O_5$: C, 67.13; H, 4.93. Found: C, 67.14; H, 5.01.

EXAMPLE 2

4-[(2,3,4,5-Tetrahydro-4-methylene-5-oxo-2-phenyl-2-furanyl)methoxy]-2H-1-benzopyran-2-one (2)

To a solution of 4-hydroxycoumarin (1.62 g, 10 mmol) in acetone (60 ml) were added 2-bromoacetophenone (1.99 g, 10 mmol) and potassium carbonate (5.53 g, 40 mmol). The mixture was refluxed for 3 h. (monitored by TLC). Evaporation of the solvent gave a residue which was poured into ice water (50 ml). The resulting solid was collected and crystallized from ethyl acetate to afford 4-(2-Oxo-2-phenylethoxy)-2H-1-benzopyran-2-one (2a) (1.76 g, 62.9%) as a needle crystal. mp: 183°–184° C.; IR(KBr) $v_{max}$: 1721, 1703, 1626; UV(CHCl$_3$) $\lambda_{max}$(log $\epsilon$): 306 (3.79), 253 (4.28); $^1$H-NMR (CDCl$_3$): δ5.50 (s, 2H, OCH$_2$), 5.61 (s, 1H, 3-H), 7.26–7.35 (m, 2H, 6- and 8-H), 7.50–7.71 (m, 4H, 5-, 7-H and aromatic H), 7.94–8.02 (m, 3H, aromatic H). Anal. Calcd for $C_{17}H_{12}O_4$: C, 72.85; H, 4.32. Found: C, 72.85; H, 4.72.

To a solution of 2a (0.84 g, 3 mmol) in dry tetrahydrofuran (60 ml) were added activated zinc powder (0.255 g, 3.9 mmol), hydroquinone (6 mg), and ethyl 2-(bromomethyl)acrylate (0.78 g, 4 mmol). The mixture was refluxed under nitrogen atmosphere for 18 h. (monitored by TLC). After cooling it was poured into an ice-cold 5% HCl solution (300 ml) and extracted with $CH_2Cl_2$ (75 ml×3). The dichloromethane extracts were combined and washed with saline, dried over $Na_2SO_4$, and then evaporated to give a residual solid which was crystallized from ethyl acetate to afford the title compound (0.90 g, 86.4%). mp: 212°–214° C.; IR(KBr) $v_{max}$: 1766, 1717, 1620; UV(CHCl$_3$) $v_{max}$(log $\epsilon$): 306 (3.89), 277 (4.10), 266 (4.14); $^1$H-NMR (CDCl$_3$): δ3.33 (dt, 1H, 4'-H), 3.66 (dt, 1H, 4'-H), 4.26, 4.32 (two d, 2H, OCH$_2$), 5.60 (s, 1H, 3-H), 5.79 (t, 1H, vinylic H), 6.42 (t, 1H, vinylic H), 7.20–7.61 (m, 9H, 5,6,7,8-H, and aromatic H). Anal. Calcd for $C_{21}H_{16}O_5·0.25H_2O$: C, 71.48; H, 4.71. Found: C, 71.37; H, 4.67.

PART B

Preparation of [(2,3,4,5-Tetrahydro-3-methylene-2-oxo-5-furanyl)methoxy]-2H-1-benzopyran-2-ones (Scheme 2)

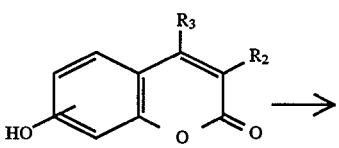

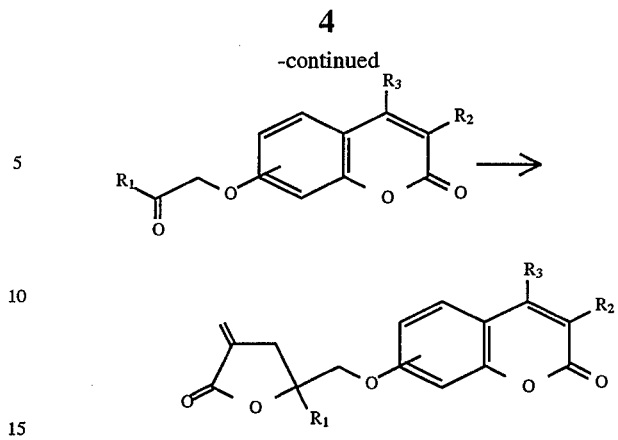

Each of the hydroxycoumarins (R$_2$=H, Cl, CH$_3$; R$_3$=H, Cl, CH$_3$) was treated with potassium carbonate and a haloketone (chloroacetone, R$_1$=CH$_3$; 2-bromoacetophenone, R$_1$=C$_6$H$_5$; 2-bromo-4'-fluoroacetophenone, R$_1$=C$_6$H$_4$F; 2-bromo-4'-chloroacetophenone, R$_1$=C$_6$H$_4$Cl; 2-bromo-4'-bromoacetophenone, R$_1$=C$_6$H$_4$Br; 2-bromo-4'-iodoacetophenone, R$_1$=C$_6$H$_4$I; 2-bromo-4'-methylacetophenone, R$_1$=C$_6$H$_4$CH$_3$; 2-bromo-4'-nitroacetophenone, R$_1$=C$_6$H$_4$NO$_2$; 2-bromo-4'-methoxyacetophenone, R$_1$=C$_6$H$_4$OCH$_3$; 2-bromo-4'-phenylacetophenone, R$_1$=C$_6$H$_4$C$_6$H$_5$) in acetone or DMF to provide (2'-oxoethoxy)-2H-1-benzopyran-2-ones which were reacted with ethyl 2-(bromomethyl)acrylate in tetrahydrofuran (THF) (Reformatsky reaction) to produce [(2,3,4,5-tetrahydro-3-methylene-2-oxo-5-furanyl)methoxy]-2H-1-benzopyran-2-ones (II).

EXAMPLE 3

7-[(2,3,4,5-Tetrahydro-2-methyl-4-methylene-5-oxo-2-furanyl)methoxy]-2H-1-benzopyran-2-one (3)

To a solution of 7-hydroxycoumarin (1.62 g, 10 mmol) in acetone (20 ml) were added potassium carbonate (5.53 g, 40 mmol) and chloroacetone (1.38 g, 15 mmol). The resulting mixture was refluxed for 4 h. (monitored by TLC). Evaporation of the solvent gave a residue which was poured into ice water (50 ml). The resulting solid was collected and crystallized from ethyl acetate to afford 7-(2-oxopropoxy)-2H-1-benzopyran-2-one (3a) (2.10 g, 96.1%) as a white needle crystal. mp: 165°–167° C.; IR(KBr) $v_{max}$: 1709, 1620; UV(CHCl$_3$) $\lambda_{max}$(log $\epsilon$): 308 (4.14), 244 (3.52); $^1$H-NMR (CDCl$_3$): δ2.31 (s, 3H, CH$_3$), 4.65 (s, 2H, OCH$_2$), 6.29 (d, 1H, 3-H), 6.76 (d, 1H, 8-H), 6.88 (dd, 1H, 6-H), 7.42 (d, 1H, 5-H), 7.65 (d, 1H, 4-H). Anal. Calcd for $C_{12}H_{10}O_4$: C, 66.05; H, 4.62. Found: C, 65.98; H, 4.61.

To a solution of 3a (0.655 g, 3 mmol) in dry tetrahydrofuran (60 ml) were added activated zinc powder (0.255 g, 3.9 mmol), hydroquinone (6 mg), and ethyl 2-(bromomethyl)acrylate (0.78 g, 4 mmol). The mixture was reflued under nitrogen atmosphere for 36 h. (monitored by TLC). After cooling it was poured into an ice-cold 5% HCl solution (300 ml) and extracted with $CH_2Cl_2$ (75 ml×3). The dichloromethane extracts were combined and washed with saline, dried over $Na_2SO_4$, and then evaporated to give a residual solid which was crystallized from ethyl acetate to afford the title compound; Yield: 79.7%; mp: 123°–124° C.; IR(KBr) $v_{max}$: 1755, 1727, 1626; UV(CHCl$_3$) $\lambda_{max}$(log $\epsilon$): 312 (4.18), 243 (3.58); $^1$H-NMR (CDCl$_3$): δ1.58 (s, 3H, 5'-CH$_3$), 2.79 (dt, 1H, 4'-H), 3.18 (dt, 1H, 4'-H), 3.99, 4.09 (two d, 2H, OCH$_2$), 5.69 (t, 1H, vinylic H), 6.26 (d, 1H, 3-H), 6.29 (t, 1H, vinylic H), 6.76–6.84 (m, 2H, 6 and 8-H).

7.38 (d, 1H, 5-H), 7.65 (d, 1H, 4-H). Anal Calcd for C$_{16}$H$_{14}$O$_5$: C, 67.13; H, 4.93. Found: C, 66.95; H, 5.10.

EXAMPLE 4

7-[(2,3,4,5-Tetrahydro-4-methylene-5-oxo-2-Phenyl-2-furanyl)methoxy]-2H-1-benzopyran-2-one (4)

To a solution of 7-hydroxycoumarin (1.62 g, 10 mmol) in acetone (60 ml) were added 2-bromoacetophenone (1.99 g, 10 mmol) and potassium carbonate (5.53 g, 40 mmol). The mixture was refluxed for 3 h. (monitored by TLC). Evaporation of the solvent gave a residue which was poured into ice water (50 ml). The resulting solid was collected and crystallized from ethyl acetate to afford 7-(2-oxo-2-phenylethoxy)-2H-1-benzopyran-2-one (4a) (1.53 g, 73.1%) as a needle crystal. mp: 163°–165° C.; IR(KBr) ν$_{max}$: 1728, 1702, 1627; UV(CHCl$_3$) λ$_{max}$(log ε): 320 (4.16), 249 (4.13); $^1$H-NMR (CDCl$_3$): δ5.39 (s, 2H, OCH$_2$), 6.27 (d, 1H, 3-H), 6.80 (d, 1H, 8-H), 6.93 (dd, 1H, 6-H), 7.40 (d, 1H, 5-H), 7.49–7.68 (m, 4H, 4-H and aromatic H). Anal Calcd for C$_{17}$H$_{12}$O$_4$: C, 72.85; H, 4.32. Found: C, 72.98; H, 4.35.

To a solution of 4a (0.84 g, 3 mmol) in dry tetrahydrofuran (60 ml) were added activated zinc powder (0.255 g, 3.9 mmol), hydroquinone (6 mg), and ethyl 2-(bromomethyl)acrylate (0.78 g, 4 mmol). The mixture was refluxed under nitrogen atmosphere for 18 h. (monitored by TLC). After cooling it was poured into an ice-cold 5% HCl solution (300 ml) and extracted with CH$_2$Cl$_2$ (75 ml×3). The dichloromethane extracts were combined and washed with saline, dried over Na$_2$SO$_4$, and then evaporated to give a residual solid which was crystallized from ethyl acetate to afford the title compound; Yield: 77.8%; mp: 105°–106° C.; IR(KBr) ν$_{max}$: 1758, 1719, 1616; UV(CHCl$_3$) λ$_{max}$(log ε): 321 (4.22), 243 (3.62); $^1$H-NMR (CDCl$_3$): δ3.24 (dt, 1H, 4'-H), 3.66(dt, 1H, 4'-H), 4.17, 4.24 (two d, 2H, OCH$_2$), 5.71 (t, 1H, vinylic H), 6.24 (d, 1H, 3-H), 6.31 (t, 1H, vinylic H), 6.72 (d, 1H, 8-H), 6.78 (dd, 1H, 6-H), 7.35 (d, 1H, 5-H), 7.40–7.52 (m, 5H, aromatic H), 7.62 (d, 1H, 4-H). Anal Calcd for C$_{21}$H$_{16}$O$_5$: C, 72.41; H, 4.63. Found: C, 72.30; H, 4.67.

PART C
Preparation of 2-Substituted [(2,3,4,5-Tetrahydro-3-methylene-2-oxo-5-furanyl)methoxy]quinolines (Scheme 3)

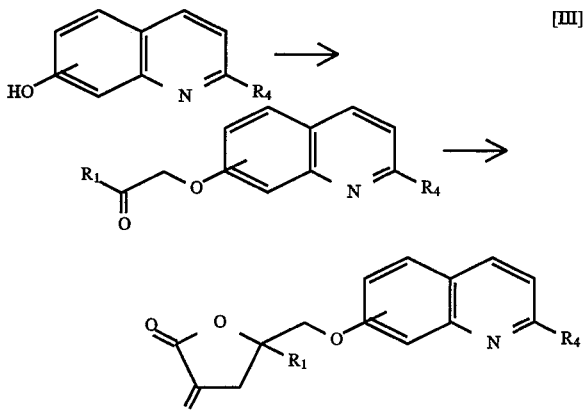

[III]

Each of the hydroxyquinolines (R$_4$=H, OH, CH$_3$) was treated with potassium carbonate and a haloketone (chloroacetone, R$_1$=CH$_3$; 2-bromoacetophenone, R$_1$=C$_6$H$_5$; 2-bromo-4'-fluoroacetophenone, R$_1$=C$_6$H$_4$F; 2-bromo-4'-chloroacetophenone, R$_1$=C$_6$H$_4$Cl; 2-bromo-4'-bromoacetophenone, R$_1$=C$_6$H$_4$Br; 2-bromo-4'-iodoacetophenone, R$_1$=C$_6$H$_4$I; 2-bromo-4'-methylacetophenone, R$_1$=C$_6$H$_4$CH$_3$; 2-bromo-4'nitroacetophenone, R$_1$=C$_6$H$_4$NO$_2$; 2-bromo-4'-methoxyacetophenone, R$_1$=C$_6$H$_4$OCH$_3$; 2-bromo-4'-phenylacetophenone, R$_1$=C$_6$H$_4$C$_6$H$_5$) in DMF or acetone to provide 2-substituted (2'-oxoethoxy)quinolines which were reacted with ethyl 2-(bromomethyl)acrylate in THF to produce 2-substituted [(2,3,4,5-tetrahydro-3-methylene-2-oxo-5-furanyl)methoxy]quinolines (III).

EXAMPLE 5

8-[(2,3,4,5-Tetrahydro-2-methyl-4-methylene-5-oxo-2-furanyl)methoxy]-2(1H)-quinolinone (5)

To a solution of 8-hydroxyquinoline (1.45 g, 10 mmol) in dichloromethane (50 ml) was added 3-chloroperbenzoic acid (MCPBA) (1.24 g, 13 mmol). The mixture was stirred at room temperature for 10 min, poured into 1.0N sodium bicarbonate (100 ml), and then extracted with dichloromethane (3×50 ml). The extract was washed with water, dried over magnesium sulfate, and evaporated to give a brown solid which was crystallized from dichloromethane and diethyl ether affording 8-Hydroxyquinoline 1-oxide (5a) (1.34 g, 83%) as yellow needle crystals. mp: 132°–133° C.; $^1$H-NMR (CDCl$_3$): δ7.04–8.28 (m, 6H, Ar—H), 15.02 (br s, 1H, OH).

A mixture of 5a (0.81 g, 5 mmol) in acetic anhydride (20 ml) was heated at reflux for 2 h (monitored by TLC). After cooling, it was poured into ice water (100 ml). The resulting solid was collected and crystallized from dichloromethane to give 2-Acetoxy-8-hydroxyquinoline (5b) (0.85 g, 84%) as white crystals. mp: 240°–241° C.; $^1$H-NMR (DMSO-d$_6$): δ2.55; (s, 3H, CH$_3$), 6.66 (d, 3-H), 7.15–7.23 (m, 3H, Ar—H), 7.78 (d, 4-H), 11.31 (br s, 1H, OH).

A mixture of 5b (1.02 g, 5 mmol), potassium carbonate (0.69 g, 5 mmol) and dry N,N-dimethylformamide (DMF) (40 ml) was stirred at room temperature for 30 min and then chloroacetone (0.46 g, 5 mmol) in dry THF (10 ml) was added in one portion. The resulting mixture was continued to stir at room temperature for 24 h (monitored by TLC). After this period, it was poured into ice water (100 ml) and the pale yellow solid thus obtained was crystallized from dichloromethane and ether to afford 2-Acetoxy-8-(2-oxopropoxy)quinoline (5c) (0.85 g, 66%). mp: 79°–80° C.; $^1$H-NMR (CDCl$_3$): δ2.16 (s, 3H, OAc), 2.42 (s, 3H, 3'-CH$_3$), 4.85 (s, 2H, OCH$_2$), 7.06 (d, 3-H), 7.26–7.67 (m, 3H, Ar—H), 8.08 (d, 4-H).

To a solution of 5c (0.78 g, 3 mmol) in dry tetrahydrofuran (60 ml) were added activated zinc powder (0.26 g, 3.9 mmol), hydroquinone (6 mg), and ethyl 2-(bromomethyl) acrylate (0.78 g, 4 mmol). The mixture was refluxed under nitrogen atmosphere for 6 h (monitored by TLC). After cooling, it was poured into an ice-cold 5% HCl solution (300 ml), neutralized with 1.0N NaHCO$_3$, and extracted with CH$_2$Cl$_2$ (75 ml×3). The dichloromethane extracts were combined and washed with water, dried over Na$_2$SO$_4$, and then evaporated to give a residual oil which was purified by column chromatography on silica gel using CH$_2$Cl$_2$ as the eluent to afford the title compound (0.59 g, 60%). UV λ$_{max}$(log ε): 258 (4.70) (0.1N HCl in MeOH), 246 (4.69) (MeOH), 261 (4.59) (0.1N NaOH in MeOH); $^1$H-NMR (CDCl$_3$): δ1.61 (s, 3H, 2'-CH$_3$), 2.78 (dt, 1H, 3'-H), 3.17 (dt, 1H, 3'-H), 4.50 (s, 2H, OCH$_2$), 5.65 (t, 1H, vinylic H), 6.29 (t, 1H, vinylic H), 6.91 (d, 1H, 3-H), 7.18–7.41 (m, 3H, Ar—H), 8.02 (d, 1H, 4-H). Anal Calcd for C$_{16}$H$_{15}$NO$_4$: C, 67.36; H, 5.30; N, 4.91. Found: C, 67.38; H, 5.32; N, 5.00.

EXAMPLE 6

8-[(2,3,4,5-Tetrahydro-4-methylene-5-oxo-2-phenyl-2-furanyl)methoxy]-2(1H)-quinolinone (6)

2-Acetoxy-8-(2-oxo-2-phenylethoxy)quinoline (6a) was prepared from 2-acetoxy-8-hydroxyquinoline (5b) and 2-bromoacetophenone by the same procedure as 5c in 74% yield. mp: 141°–142° C.; $^1$H-NMR (CDCl$_3$): δ1.92 (s, 3H, CH$_3$), 5.66 (s, 2H, OCH$_2$), 7.11 (d, 3-H), 7.25–8.04 (m, 8H, Ar—H), 8.05 (d, 4-H).

The title compound was prepared from 6a by the same procedure as 5 in 57% yield. UV $\lambda_{max}$(log ε): 260 (4.69) (0.1N HCl in MeOH), 247 (4.73) (MeOH), 261 (4.61) (0.1N NaOH in MeOH); $^1$H-NMR (CDCl$_3$): δ3.23 (dt, 1H, 3'-H), 3.63 (dt, 1H, 3'-H), 4.63 (d, 1H, OCH), 4.71 (d, 1H, OCH), 5.66 (t, 1H, vinylic H), 6.30 (t, 1H, vinylic H), 6.88 (d, 1H, 3-H), 7.15–7.52 (m, 8H, Ar—H), 8.00 (d, 1H, 4-H). Anal. Calcd for C$_{21}$H$_{17}$NO$_4$: C, 72.61; H, 4.93; N, 4.03. Found: C, 72.69; H, 4.94; N, 4.11.

EXAMPLE 7

8-[(2,3,4,5-Tetrahydro-2-methyl-4-methylene-5-oxo-2-furanyl)methoxy]quinoline (7)

8-Hydroxyquinoline (0.73 g, 5 mmol), potassium carbonate (0.69 g, 5 mmol) and dry N,N-dimethylformamide (DMF) (40 ml) were stirred at room temperature for 30 min. To this solution was added chloroacetone (0.46 g, 5 mmol) in dry THF (10 ml) in one portion. The resulting mixture was stirred at room temperature for 24 h. (monitored by TLC) and then poured into ice water (100 ml). The pale yellow solid thus obtained was collected and crystallized from dichloromethane and ether to afford 8-(2-oxopropoxy)quinoline (7a) (0.68 g, 67%) as a pale yellow needle crystal. mp: 58°–59° C.; $^1$H-NMR (CDCl$_3$): δ2.32 (s, 3H, CH$_3$), 4.88 (s, 2H, OCH$_2$), 6.88–8.97 (m, 6H, Ar—H).

To a solution of 7a (0.60 g, 3 mmol) in dry tetrahydrofuran (60 ml) were added activated zinc powder (0.26 g, 3.9 mmol), hydroquinone (6 mg), and ethyl 2-(bromomethyl) acrylate (0.78 g, 4 mmol). The mixture was refluxed under nitrogen atmosphere for 6 h (monitored by TLC). After cooling, it was poured into an ice-cold 5% HCl solution (300 ml), neutralized with 1.0N NaHCO$_3$, and extracted with CH$_2$Cl$_2$ (60 ml×3). The dichloromethane extracts were combined and washed with water, dried over Na$_2$SO$_4$, and then evaporated to give a residual oil which was purified by column chromatography on silica gel using CH$_2$Cl$_2$ as the eluent to afford the title compound (0.66 g, 82%). UV $\lambda_{max}$(log ε): 250 (4.69) (0.1N HCl in MeOH), 237 (4.60) (MeOH), 238 (4.64) (0.1N NaOH in MeOH); $^1$H-NMR (CDCl$_3$): δ1.61 (s, 3H, 2'-CH$_3$), 2.84 (dt, 1H, 3'-H), 3.48 (dt, 1H, 3'-H), 4.25 (d, 1H, OCH), 4.32 (d, 1H, OCH), 5.66 (t, 1H, vinylic H), 6.26 (t, 1H, vinylic H), 7.13–8.91 (m, 6H, Ar—H). Anal. Calcd for C$_{16}$H$_{15}$NO$_3$.⅛H$_2$O: C, 70.77; H, 5.65; N, 5.16. Found: C, 70.80; H, 5.75; N, 5.08.

EXAMPLE 8

8-[(2,3,4,5-Tetrahydro-4-methylene-5-oxo-2-phenyl-2-furanyl)methoxy]quinoline (8)

8-(2-Oxo-2-phenylethoxy)quinoline (8a) was prepared from 2-bromoacetophenone by the same procedure as 7a in 69% yield. mp: 124°–125° C.; $^1$H-NMR (CDCl$_3$): δ5.65 (s, 2H, OCH$_2$), 6.95–8.97 (m, 11H, Ar—H).

The title compound was prepared from 8a by the same procedure as 7 in 75% yield. mp: 101°–102° C.; UV $\lambda_{max}$(log ε): 250 (4.69) (0.1N HCl in MeOH), 237 (4.62) (MeOH), 237 (4.67) (0.1N NaOH in MeOH); $^1$H-NMR (CDCl$_3$): δ3.25 (dt, 1H, 3'-H), 4.09 (dt, 1H, 3'-H), 4.46 (d, 1H, OCH), 4.62 (d, 1H, OCH), 5.68 (t, 1H, vinylic H), 6.25 (t, 1H, vinylic H), 7.16–8.90 (m, 11H, Ar—H). Anal. Calcd for C$_{21}$H$_{17}$NO$_3$: C, 76.11; H, 5.17; N, 4.23. Found: C, 76.10; H, 5.19; N, 4.27.

EXAMPLE 9

8-[(2-(p-Chlorophenyl)-2,3,4,5-tetrahydro-4-methylene-5-oxo-2-furanyl)methoxy]quinoline (9)

8-(2-(p-Chlorophenyl)-2-oxoethoxy)quinoline (9a) was prepared from 2-bromo-4'-chloroacetophenone by the same procedure as 7a in 76% yield. mp: 111°–112° C.; $^1$H-NMR (CDCl$_3$): δ5.56 (s, 2H, OCH$_2$), 6.96–8.96 (m, 10 H, Ar—H).

The title compound was prepared from 9a by the same procedure as 7 in 69% yield. mp: 107°–108° C.; UV $\lambda_{max}$(log ε): 249 (4.75) (0.1N HCl in MeOH), 236 (4.69) (MeOH), 238 (4.28) (0.1N NaOH in MeOH); $^1$H-NMR (CDCl$_3$): δ3.20 (dt, 1H, 3'-H), 4.06 (dt, 1H, 3'-H), 4.42 (d, 1H, OCH), 4.56 (d, 1H, OCH), 5.70 (t, 1H, vinylic H), 6.28 (t, 1H, vinylic H), 7.13–8.91 (m, 10H, Ar—H). Anal. Calcd for C$_{21}$H$_{16}$ClNO$_3$: C, 68.95; H, 4.41; N, 3.83. Found: C, 68.91; H, 4.44; N, 3.87.

EXAMPLE 10

8-[(2,3,4,5-Tetrahydro-2-methyl-4-methylene-5-oxo-2-furanyl)methoxy]-2-methylquinoline (10)

2-Methyl-8-hydroxyquinoline (0.80 g, 5 mmol), potassium carbonate (0.69 g, 5 mmol) and dry N,N-dimethylformamide (DMF) (40 ml) were stirred at room temperature for 30 min. To this solution was added chloroacetone (0.46 g, 5 mmol) in dry THF (10 ml) in one portion. The resulting mixture was stirred at room temperature for 24 h. (monitored by TLC) and then poured into ice water (100 ml). The pale yellow solid thus obtained was collected and crystallized from dichloromethane and ether to afford 2-methyl-8-(2-oxopropoxy)quinoline (10a) (0.77 g, 72%). mp: 99°–100° C.; $^1$H-NMR (CDCl$_3$): δ2.35 (s, 3H, 2'-CH$_3$), 2.79 (s, 3H, 2-CH$_3$), 4.86 (s, 2H, OCH$_2$), 6.88–7.44 (m, 3H, Ar—H), 7.33 (d, 1H, 3-H), 8.03 (d, 1H, 4-H).

The title compound was prepared from 10a by the same procedure as 7 in 70% yield. UV $\lambda_{max}$(log ε): 253 (4.42) (0.1N HCl in MeOH), 238 (4.45) (MeOH), 239 (4.46) (0.1N NaOH in MeOH); $^1$H-NMR (CDCl$_3$): δ1.61 (s, 3H, 2'-CH$_3$), 2.71 (s, 3H, 2-CH$_3$), 2.80 (dt, 1H, 3'-H), 3.53 (dt, 1H, 3'-H), 4.24 (d, 1H, OCH), 4.30 (d, 1H, OCH), 5.67 (t, 1H, vinylic H), 6.28 (t, 1H, vinylic H), 7.08–7.42 (m, 3H, Ar—H), 7.26 (d, 1H, 3-H), 7.97 (d, 1H, 4-H). Anal. Calcd for C$_{17}$H$_{17}$NO$_3$.⅛H$_2$O: C, 71.50; H, 6.09; N, 4.90. Found: C, 71.26; H, 6.13; N, 4.73.

EXAMPLE 11

8-[(2,3,4,5-Tetrahydro-4-methylene-5-oxo-2-phenyl-2-furanyl)methoxy]-2-methylquinoline (11)

2-Methyl-8-(2-oxo-2-phenylethoxy)quinoline (11a) was prepared from 2-bromoacetophenone by the same procedure as 10a in 72% yield. mp: 70°–71° C.; $^1$H-NMR (CDCl$_3$): δ2.77 (s, 3H, 2-CH$_3$), 5.63 (s, 2H, OCH$_2$), 6.94–8.10 (m, 8H, Ar—H), 7.29 (d, 1H, 3-H), 7.99 (d, 1H, 4-H).

The title compound was prepared from 11a by the same procedure as 7 in 61% yield. mp: 108°–109° C.; UV $\lambda_{max}$(log ε): 253 (4.53) (0.1N HCl in MeOH), 239 (4.46) (MeOH), 240 (4.51) (0.1N NaOH in MeOH); $^1$H-NMR (CDCl$_3$): δ2.74 (s, 3H, CH$_3$), 3.25 (dt, 1H, 3'-H), 4.12 (dt, 1H, 3'-H), 4.41 (d, 1H, OCH), 4.56 (d, 1H, OCH), 5.71 (t, 1H, vinylic H), 6.31 (t, 1H, vinylic H), 7.06–7.60 (m, 8H, Ar—H), 7.27 (d, 1H, 3-H), 7.98 (d, 1H, 4-H). Anal. Calcd for C$_{22}$H$_{19}$NO$_3$: C, 76.51; H, 5.54; N, 4.06. Found: C, 76.52; H, 5.55; N, 4.15.

EXAMPLE 12

8-[(2-(p-Chlorophenyl)-2,3,4,5-tetrahydro-4-methylene-5-oxo-2-furanyl)methoxy]-2-methylquinoline (12)

8-(2-(p-Chlorophenyl)-2-oxoethoxy)-2-methylquinoline (12a) was prepared from 2-bromo-4'-chloroacetophenone by the same procedure as 10a in 64% yield. mp: 112°–113° C.; $^1$H-NMR (CDCl$_3$): δ2.77 (s, 3H, 2-CH$_3$), 5.56 (s, 2H, OCH$_2$), 6.94–8.12 (m, 8H, Ar—H), 7.31 (d, 1H, 3-H), 8.00 (d, 1H, 4-H).

The title compound was prepared from 12a by the same procedure as 7 in 68% yield. mp: 129°–130° C.; UV $\lambda_{max}$(log ε): 253 (4.62) (0.1N HCl in MeOH), 238 (4.60) (MeOH), 240 (4.61) (0.1N NaOH in MeOH); $^1$H-NMR (CDCl$_3$): δ2.74 (s, 3H, CH$_3$), 3.20 (dt, 1H, 3'-H), 4.08 (dt, 1H, 3'-H), 4.37 (d, 1H, OCH), 4.50 (d, 1H, OCH), 5.72 (t, 1H, vinylic H), 6.32 (t, 1H, vinylic H), 7.04–7.58 (m, 7H, Ar—H), 7.27 (d, 1H, 3H), 7.98 (d, 1H, 4-H). Anal. Calcd for C$_{22}$H$_{18}$ClNO$_3$: C, 69.56; H, 4.78; N, 3.69. Found: C, 69.51; H, 4.79; N, 3.75.

PART D: Antiplatelet activity

The pharmacological activity of these compounds were determined according to G.V.R. Born by turbidimetry (*J. Physiol.*, 1963, 168, 178). Based on the method, samples were suspended in rabbit platelets which were washed with platelet-rich plasma, the aggregation was then counted by the Lumi-aggregometer (Model 1020, Paytoon, Canada). The results are shown in Table 1. Formula (I–III) at the concentration of 100 µg/ml are found to inhibit the platelet aggregation perfectly which was induced by arachidonic acid (AA), collagen, ADP, and PAF. Since the structures of these compounds are different from those of known antiplatelet agents, the present invention have the potential for further development.

Compounds of this invention may be administered parenterally or orally in a suitable pharmaceutical form. They also may be administered along or in conjunction with other antiplatelet agents, in combination with any pharmaceutically acceptable carrier.

As used herein, suitable pharmaceutical forms include sterile aqueous solutions or dispersions, sterile powders, tablets, troches, pills, capsules, and the like. In addition, the active compounds may be incorporated into sustained-release preparations and formulations. The pharmaceutically acceptable carrier for oral dosage form are, in particular, filers, such as sugars, for example, lactose, sucrose, mannitol, and furthermore binders, such as starch mucilage using, for example, wheat, rice or potato starch, and/or, if desired, disintegrating or adjuncts. Those carriers for parenteral dosage form are, in particular, aqueous solutions and furthermore lipophilic solvents or vehicles such as fatty oils, and/or, if desired, viscosity-increasing substance, for example sodium carboxymethyl cellulose, sorbitol.

Although the compound of the present invention may also be present as a hydrate or as a stereoisomer, it is a matter of course that these hydrates and stereoisomers are also included in the scope of the present invention. The prefer individual dose is 50 to 300 mg for oral administration and 2 to 15 mg for intravenous administration and can be administered up to 3 times daily.

(A) Preparation of platelet aggregation inducers:

1. Bovine thrombin, from the Parke Davis Co., was dissolved in 50% (v/v) glycerol for a stock solution of 100 NIH units/mL.

2. Collagen (type I: bovine Achilles tendon), from the Sigma Chemical Co., was homogenized in 25 mM acetic acid and stored (1 mg/mL) at −70° C.

3. PAF (1-O-alkyl-2-acetyl-sn-glycerol-3-phosphorylcholine), purchased from Sigma, was dissolved in chloroform and diluted into 0.1% BSA-saline solution immediately prior to use.

4. AA (arachidonic acid), purchased from Sigma, was dissolved in deionized water.

(B) Preparation of platelets:

Platelet suspension was prepared from EDTA-anticoagulated Platelet-rich plasma according to washing procedures described previously (Teng, C. M. et. al., *Thromb Haemost* 59, 304, 1991). Platelets were counted by Hemalaser 2 (Sebia, France) and adjusted to a concentration of 4.5×10$^8$ platelets/mL. Platelet pellets were finally suspended in Tyrode's buffer (pH 7.4) of the following composition: NaCl (136.8 mM), KCl (2.8 mM), NaHCO$_3$ (11.9 mM), MgCl$_2$ (2.1 mM), NaH$_2$PO4 (0.33 mM), CaCl$_2$ (1 mM), glucose (11.2 mM) containing 0.35% bovine serum albumin.

(C) Platelet aggregation and ATP release reaction:

Aggregation was measured by the turbidimetry method as described by O'Brien (*J Clin Pathol* 15, 452, 1962). ATP released from platelets was detected by the bioluminescence method of DeLuca and McElory (*Methods Enzymol* 57, 3, 1978). Both aggregation and ATP release were measured simultaneously in a Lumi-aggregometer (model 1020B, Payton, Canada) connected to two dt/al-channel recorders. Platelet preparations were stirred at 900 rpm. When DMSO was used as solvent, its final concentration was fixed at 0.5% (v/v) to eliminate the effect of the solvent. For the calculation of percentage aggregation, the absorbance of platelet suspension was designated as 0% aggregation and the absorbance of platelet-free Tyrode's solution as 100% aggregation. The antiplatelet effects were shown in Table 1 and the inhibitory concentrations for 50% aggregation (IC$_{50}$) were expressed in Table 2.

BRIEF DESCRIPTION OF THE DRAWING

Table 1. Effect of α-methylene-γ-butyrolactones on the platelet aggregation (%) induced by thrombin (Thr), arachidonic acid (AA), collagen (Col) and platelet-activating factor (PAF) in washed rabbit platelets[a]

Table 2. IC$_{50}$ values of α-methylene-γ-butyrolactones on the platelet aggregation induced by Thr (0.1 U/ml), AA (100 µg/ml), Col (10 µg/ml), and PAF (2 nM)

TABLE 1

Effect of α-methylene-γ-butyrolactones on the platelet aggregation (%) induced by thrombin (Thr), arachidonic acid (AA), collagen (Col) and platelet-activating factor (PAF) in washed rabbit platelets[a]

| | Inducer | | | |
|---|---|---|---|---|
| Compds | Thr 0.1 U/ml | AA 100 µM | Col 10 µg/ml | PAF 2 nM |
| Control | 91.7 ± 1.0(5) | 86.4 ± 1.0(5) | 89.2 ± 1.4(5) | 88.2 ± 0.8(4) |
| 1 | 74.4 ± 9.6(4) | 23.3 ± 12.6(4)[b] | 8.5 ± 6.9(3)[b] | 33.6 ± 16.6(5)[b] |
| 2 | 0.0 ± 0.0(4) | 0.0 ± 0.0(3) | 0.0 ± 0.0(3) | 0.0 ± 0.0(4)[b] |
| 3 | 22.8 ± 6.6(4)[b] | 0.0 ± 0.0(4)[b] | 0.0 ± 0.0(3)[b] | 0.0 ± 0.0(3)[b] |

TABLE 1-continued

Effect of α-methylene-γ-butyrolactones on the platelet aggregation (%) induced by thrombin (Thr), arachidonic acid (AA), collagen (Col) and platelet-activating factor (PAF) in washed rabbit platelets[a]

| Compds | Inducer | | | |
|---|---|---|---|---|
| | Thr 0.1 U/ml | AA 100 μM | Col 10 μg/ml | PAF 2 nM |
| Control | 91.7 ± 1.0(5) | 86.4 ± 1.0(5) | 89.2 ± 1.4(5) | 88.2 ± 0.8(4) |
| 4 | 0.0 ± 0.0(3)[b] | 0.0 ± 0.0(4)[b] | 0.0 ± 0.0(3) | 0.0 ± 0.0(3)[b] |
| 5 | 25.9 ± 0.7(3)[b] | 0.0 ± 0.0(3)[b] | 0.0 ± 0.0(3)[b] | 7.0 ± 1.1(3)[b] |
| 6 | 54.3 ± 1.3(3)[b] | 0.0 ± 0.0(3)[b] | 0.0 ± 0.0(3)[b] | 42.2 ± 1.3(3)[b] |
| 7 | 17.4 ± 7.9(3)[b] | 0.0 ± 0.0(4)[b] | 0.0 ± 0.0(4)[b] | 0.0 ± 0.0(4)[b] |
| 8 | 0.0 ± 0.0(4)[b] | 0.0 ± 0.0(4)[b] | 0.0 ± 0.0(4)[b] | 0.0 ± 0.0(4)[b] |
| 9 | 0.0 ± 0.0(3)[b] | 0.0 ± 0.0(4)[b] | 0.0 ± 0.0(4)[b] | 0.0 ± 0.0(3)[b] |
| 10 | 0.0 ± 0.0(3)[b] | 0.0 ± 0.0(4)[b] | 0.0 ± 0.0(4)[b] | 0.0 ± 0.0(3)[b] |
| 11 | 0.0 ± 0.0(4)[b] | 0.0 ± 0.0(4)[b] | 0.0 ± 0.0(4)[b] | 0.0 ± 0.0(4)[b] |
| 12 | 0.0 ± 0.0(3)[b] | 0.0 ± 0.0(3)[b] | 0.0 ± 0.0(3)[b] | 0.0 ± 0.0(3)[b] |

[a]Platelets were preincubated with DMSO (0.5%, control) or (α-methylene-γ-butyrolactones (100 μg/ml) at 37° for 3 min, and the inducer was then added. Percentages of aggregation are presented as means ± standard errors of the mean (n).
[b]Significantly different from control value at $p < 0.001$.

TABLE 2

$IC_{50}$ values of α-methylene-γ-butyrolactones on the platelet aggregation induced by Thr (0.1 U/ml), AA (100 μg/ml), Col (10 μg/ml), and PAF (2 nM)

| Compds | $IC_{50}$ (μg/ml) | | | |
|---|---|---|---|---|
| | Thr | AA | Col | PAF |
| 1 | >50 | >50 | >50 | >50 |
| 2 | ND[a] | 2.86 | ND | 36.01 |
| 3 | >50 | 26.08 | ND | >50 |
| 4 | ND | 1.27 | ND | 5.70 |
| 5 | ND | 10.53 | ND | ND |
| 6 | >50 | 8.30 | ND | >50 |
| 7 | >50 | 23.91 | 27.25 | 47.86 |
| 8 | 15.78 | 4.70 | 4.76 | 11.13 |
| 9 | 13.69 | 6.31 | 5.17 | 12.37 |
| 10 | >50 | 17.51 | 16.24 | 39.56 |
| 11 | 14.88 | 4.44 | 5.76 | 10.54 |
| 12 | ND | 4.19 | ND | 10.82 |

[a]Not Determined

We claim:

1. A compound represented by the general formula I–III as follow:

[Structural formulas I, II, and III showing α-methylene-γ-butyrolactone derivatives with coumarin and quinoline moieties]

For the formula I, $R_1$ is a methyl, a phenyl group optionally substituted with one or two group selected from halide, ($C_1$–$C_4$) alkyl, ($C_1$–$C_4$) alkoxy, phenyl, nitro, amino;

For the formula II, $R_1$ is a methyl, a phenyl group optionally substituted with one or two group selected from halide, ($C_1$–$C_4$) alkyl, ($C_1$–$C_4$) alkoxy, phenyl, nitro, amino; $R_2$ represents hydrogen, halide, ($C_1$–$C_4$) alkyl, phenyl, nitro, amino; $R_3$ represents hydrogen, halide, ($C_1$–$C_4$) alkyl, phenyl, nitro, amino;

For the formula III, $R_1$ is a methyl, a phenyl group optionally substituted with one or two group selected from halide, ($C_1$–$C_4$) alkyl, ($C_1$–$C_4$) alkoxy, phenyl, nitro, amino; $R_4$ represents hydrogen, hydroxy, ($C_1$–$C_4$) alkyl.

2. A compound as claim 1, formula I, wherein $R_1$ is a methyl, a phenyl group optionally substituted with one or two group selected from halide, ($C_1$–$C_4$) alkyl, ($C_1$–$C_4$) alkoxy, phenyl, nitro, amino.

3. A compound as claim 1, formula II, wherein $R_1$ is a methyl, a phenyl group optionally substituted with one or two group selected from halide, ($C_1$–$C_4$) alkyl, ($C_1$–$C_4$) alkoxy, phenyl, nitro, amino; $R_2$ represents hydrogen, halide, ($C_1$–$C_4$) alkyl, phenyl, nitro, amino; $R_3$ represents hydrogen, halide, ($C_1$–$C_4$) alkyl, phenyl, nitro, amino.

4. A compound as claim 1, formula III, wherein $R_1$ is a methyl, a phenyl group optionally substituted with one or two group selected from halide, ($C_1$–$C_4$) alkyl, ($C_1$–$C_4$) alkoxy, phenyl, nitro, amino; $R_4$ represents hydrogen, hydroxy, ($C_1$–$C_4$) alkyl.

5. A method of treating platelet aggregation in an animal comprising the steps of administrating any compound of claim 1 or their pharmaceutically acceptable salts in an amount effective to inhibit platelet aggregation.

* * * * *